(12) United States Patent
Yu

(10) Patent No.: US 8,025,869 B2
(45) Date of Patent: Sep. 27, 2011

(54) COSMETIC COMPOSITIONS HAVING ENHANCED WEAR PROPERTIES

(75) Inventor: Wei Hong Yu, Edison, NJ (US)

(73) Assignee: L'Oréal (FR)

( * ) Notice: Subject to any disclaimer, the term of this patent is extended or adjusted under 35 U.S.C. 154(b) by 1037 days.

(21) Appl. No.: 11/168,796

(22) Filed: Jun. 28, 2005

(65) Prior Publication Data

US 2006/0292096 A1    Dec. 28, 2006

(51) Int. Cl.
*A61K 8/00* (2006.01)
*A61K 8/18* (2006.01)

(52) U.S. Cl. ........ 424/61; 424/400; 424/70.11; 424/401

(58) Field of Classification Search .................. None
See application file for complete search history.

(56) References Cited

U.S. PATENT DOCUMENTS

| | | | |
|---|---|---|---|
| 3,148,125 A | 9/1964 | Strianse et al. | |
| 3,645,705 A | 2/1972 | Miller et al. | |
| 4,574,082 A | 3/1986 | Tietjen et al. | |
| 5,266,321 A | 11/1993 | Shukuzaki et al. | |
| 5,500,209 A | 3/1996 | Mendolia et al. | |
| 5,505,937 A | 4/1996 | Castrogiovanni et al. | |
| 5,783,657 A | 7/1998 | Pavlin et al. | |
| 5,849,318 A | 12/1998 | Imai et al. | |
| 5,911,974 A | 6/1999 | Brieva et al. | |
| 5,948,393 A | 9/1999 | Tomomasa et al. | |
| 5,965,112 A | 10/1999 | Brieva et al. | |
| 5,985,298 A | 11/1999 | Brieva et al. | |
| 5,998,570 A | 12/1999 | Pavlin et al. | |
| 6,074,654 A | 6/2000 | Drechsler et al. | |
| 6,268,466 B1 | 7/2001 | MacQueen et al. | |
| 6,342,209 B1 * | 1/2002 | Patil et al. | 424/61 |
| 6,372,235 B1 | 4/2002 | Livoreil et al. | |
| 6,402,408 B1 | 6/2002 | Ferrari | |
| 6,406,683 B1 | 6/2002 | Drechsler et al. | |
| 6,440,430 B1 | 8/2002 | Bara et al. | |
| 6,552,160 B2 | 4/2003 | Pavlin | |
| 6,620,417 B1 | 9/2003 | Jose et al. | |
| 6,726,195 B1 | 4/2004 | Hertz et al. | |
| 6,780,422 B2 | 8/2004 | Brieva et al. | |
| 2002/0031488 A1 | 3/2002 | Kanji et al. | |
| 2002/0058054 A1 | 5/2002 | Arnaud | |
| 2002/0114773 A1 | 8/2002 | Kanji et al. | |
| 2002/0159960 A1 | 10/2002 | Scancarella et al. | |
| 2003/0039620 A1 | 2/2003 | Rodriguez et al. | |
| 2003/0067545 A1 | 4/2003 | Giron et al. | |
| 2003/0068348 A1 | 4/2003 | Ferrari et al. | |
| 2003/0082125 A1 | 5/2003 | Grimm | |
| 2003/0185780 A1 | 10/2003 | Ferrari et al. | |
| 2004/0009137 A1 | 1/2004 | Wyatt | |
| 2004/0064509 A1 | 4/2004 | Ayyagari et al. | |
| 2004/0071648 A1 | 4/2004 | Delacour et al. | |
| 2004/0156806 A1 | 8/2004 | Patil et al. | |
| 2004/0180011 A1 | 9/2004 | Schlosser | |
| 2004/0191201 A1 | 9/2004 | Maio et al. | |
| 2005/0008598 A1 | 1/2005 | Lu et al. | |

FOREIGN PATENT DOCUMENTS

| | | |
|---|---|---|
| EP | 0 134 264 | 3/1985 |
| EP | 0 295 886 | 12/1988 |
| EP | 0 749 747 | 12/1996 |
| EP | 0 815 836 | 1/1998 |
| EP | 0 862 411 | 9/1998 |
| EP | 0 950 401 | 10/1999 |
| EP | 1 002 528 | 5/2000 |
| EP | 1 040 821 | 10/2000 |
| EP | 1 184 028 | 3/2002 |
| WO | 00/64401 | 11/2000 |
| WO | 02/17861 | 3/2002 |
| WO | 02/41854 | 5/2002 |
| WO | 02/053126 | 7/2002 |
| WO | 02/067877 | 9/2002 |
| WO | 02/072044 | 9/2002 |
| WO | 02/072045 | 9/2002 |
| WO | 02/072046 | 9/2002 |
| WO | 02/080863 | 10/2002 |
| WO | 02/089760 | 11/2002 |
| WO | 03/086333 | 10/2003 |
| WO | 03/105801 | 12/2003 |
| WO | 2004/071444 | 8/2004 |

OTHER PUBLICATIONS

Capresse et al. A new silicone resin for personal care applications, published in 2004.*
"Specialist Surfactants" edited by D. Robb, 1997, pp. 209-263, chapter 8, by P. Terech.
Dow Corning® 670 Fluid—Intellectual Property Statement, Factsheet, Apr. 2005.
Dow Corning®—Research Disclosure—A New Silicone Resin for Personal Care Applications, Oct. 2004.

* cited by examiner

*Primary Examiner* — Anand Desai
*Assistant Examiner* — Melissa Mercier
(74) *Attorney, Agent, or Firm* — Lerner, David, Littenberg, Krumholz & Mentlik, LLP

(57) ABSTRACT

A cosmetic composition and process which provides enhanced wear and transfer resistance containing: (a) at least one polypropylsilsesquioxane film forming resin; (b) at least one solvent; and (c) optionally, at least one colorant.

20 Claims, No Drawings

COSMETIC COMPOSITIONS HAVING ENHANCED WEAR PROPERTIES

BACKGROUND OF THE INVENTION

The present invention relates to a cosmetic composition, especially a makeup and/or care composition for keratinous materials comprising a silicone resin in a cosmetically acceptable medium. The invention also relates to a makeup process or care process for the keratinous materials.

The use of film-forming silicone resins in cosmetic compositions has been described, for example, in U.S. Pat. No. 5,505,937, U.S. Pat. No. 5,911,974, U.S. Pat. No. 5,965,112, U.S. Pat. No. 5,985,298, U.S. Pat. No. 6,074,654, US20020031488, U.S. Pat. No. 6,780,422, US20040156806. These patents and patent applications describe and claim compositions containing various silicone resins in association with several specific ingredients. The presence of these silicone resins makes it possible to increase the wear of the composition applied to the skin, lips or lashes. However, while these cosmetic compositions are drying on the skin, they often give rise to sensations of tautness that the user finds unpleasant, making the composition uncomfortable to wear. These problems of comfort are especially associated with the mechanical properties of the deposits obtained on the skin. In particular, when the film formed on the skin after applying the composition is too rigid, it leaves an unpleasant sensation, for example during movements of the face.

Although the use of silicone resins, in general, does increase the wear of cosmetic compositions due to their ability to form films, the rigidity of the film may cause it to flake off from the keratinous substrate onto which it is applied, thereby reducing its wear properties.

There is thus still a need for a stable cosmetic composition to be applied to the skin, which forms a film that is both comfortable on the skin and shows good wear properties in terms of its resistance to flaking. It has been unexpectedly discovered that such a composition may be obtained by using a specific type of silsesquioxane film forming resin in a cosmetically acceptable medium.

Surprisingly, the Applicant has found that such a composition containing a polypropylsilsesquioxane film forming resin in a cosmetically acceptable medium gives a deposit on the skin that shows noteworthy cosmetic properties. In particular, such a composition is comfortable to apply and shows good wear properties, especially good resistance to flaking. The use of this polypropylsilsesquioxane film forming resin can also obviate the use of a plasticizer.

SUMMARY OF THE INVENTION

The present invention relates to a cosmetic composition providing long wear containing:
a) at least one polypropylsilsesquioxane film forming resin;
b) at least one solvent; and
c) optionally, at least one colorant.

The invention also relates to a process for treating a keratinous material involving contacting the keratinous material with a cosmetic composition containing:
a) at least one polypropylsilsesquioxane film forming resin;
b) at least one solvent; and
c) optionally, at least one colorant.

DETAILED DESCRIPTION

Other than in the operating examples, or where otherwise indicated, all numbers expressing quantities of ingredients and/or reaction conditions are to be understood as being modified in all instances by the term "about".

It has been unexpectedly discovered that a cosmetic composition containing at least one polypropylsilsesquioxane film forming resin provides enhanced wear properties.

Without intending to be bound by theory, it is believed that the propyl substituted polymeric silsesquioxane film forming resin utilized in a cosmetically acceptable composition provides a more flexible, homogeneous, and less rigid film on the keratinous material resulting in comfortable, and extended wear.

The invention may be used as an eyeshadow, an eyeliner, a blush, a foundation, a mascara, or a lip composition. In addition, the product of the invention, instead of being molded in the form of a stick, may also be hot-poured.

The term "keratinous material" is meant to include hair and skin.

By the term "resin" it is meant that the polypropylsilsesquioxane film forming polymer provides substantive, film forming properties when applied to skin.

The term "film forming" means that the polypropylsilsesquioxane polymer is capable of forming a film, in particular, a substantive film, on the keratinous surface to which it is applied.

Moreover, by "comprising" it is meant that other steps and/or ingredients which do not affect the end result may be added. The products, compositions, methods and processes of the present invention can include all the essential elements and limitations of the invention described herein as well as any of the additional or optional ingredients, components, steps, or limitations described herein.

All percentages, parts and ratios are based upon the total weight of the compositions of the present invention unless otherwise indicated.

The compositions and processes, including the essential and additional or optional components are described in detail below.

Polypropylsilsesquioxane Film-Forming Resins

Silsesquioxane resins are a specific form of silicone resins. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure:

Structure 1

At least one of the methyl groups of the M unit may be replaced by another group, e.g., to give a unit with formula $[R(CH_3)_2]SiO_{1/2}$, as represented in the following structure:

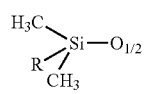

Structure 2 wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

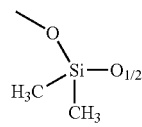

Structure 3

Here again, at least one of the methyl groups of the D unit may be replaced by another group, e.g., to give a unit with formula $R_a R_b SiO_{2/2}$, $RCH_3 SiO_{2/2}$ or wherein $R_a$ and $R_b$ may be chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol T denotes the trifunctional unit, $CH_3SiO_{3/2}$ and can be represented as:

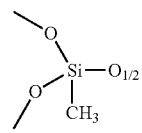

Structure 4

Here again, the methyl group may be replaced by another group, e.g., to give a unit with formula $RSiO_{3/2}$, wherein R may be chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, phenyl groups, alkoxy groups, wherein the groups other than methyl groups may be further substituted.

Similarly, the symbol Q denotes the tetrafunctional unit, $SiO_{4/2}$ wherein all four oxygens bonded to the silicone atom are bonded to the rest of the polymer.

When the film forming resin is made up predominantly of trifunctional units or T units, it is generally called a silsesquioxane resin. If it is made up primarily of repeating units as depicted in Structure 4, it is called a polymethylsilsesquioxane. A non-limiting example of the at least one polymethylsilsesquioxane film former is Belsil PMS MK, also referred to as Resin MK, available from Wacker Chemie. This polymethylsilsesquioxane film former is a polymer comprising polymerized repeating units of $CH_3SiO_{3/2}$ (T units) and may also contain up to 1% by weight or by mole of units of the formula $(CH_3)_2SiO_{2/2}$ (D units). The weight-average molecular weight of this polymer has been estimated to be 10,000.

When the film forming resin is made up predominantly of trifunctional $RSiO_{3/2}$ units or T units, wherein R is a propyl radical, it is called a polypropylsilsesquioxane.

One example of a polypropylsilsesquioxane resin suitable for use in the present invention is commercially available from Dow-Corning as Dow Corning 670 Fluid. Dow Corning 670 Fluid has a general formula of $R_n SiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight.

The film forming polypropylsilsesquioxane resin may be present in an amount ranging from 0.5 to 80% by weight, preferably from 5 to 70% by weight, more preferably from 10 to 50% by weight, more preferably from 15 to 40% by weight, and more preferably from 20 to 30% by weight, based on the weight of the total composition.

The Solvent

The at least one solvent for use in the present invention may be chosen from volatile solvents and non-volatile solvents.

Volatile Solvents

The expression "volatile solvent" means any nonaqueous medium capable of evaporating from the keratinous material, at room temperature. This volatile phase in particular comprises oils with a vapor pressure at room temperature and at atmospheric pressure ranging from 0.13 Pa to 40 000 Pa ($10^{-3}$ to 300 mm Hg). These volatile oils especially facilitate the application of the composition to the skin. These oils may be hydrocarbon-based oils, silicone oils (optionally comprising alkyl or alkoxy groups that are pendant or at the end of a silicone chain), and fluoro oils.

As volatile silicone oils, mention may be made of linear or cyclic silicones containing from 2 to 7 silicon atoms, these silicones optionally comprising alkyl or alkoxy groups containing from 1 to 10 carbon atoms. Mention may thus be made especially of octamethylcyclotetrasiloxane, decamethylcyclopentasiloxane, hexadecamethylcyclohexasiloxane, heptamethylhexyltrisiloxane and heptamethyloctyltrisiloxane, and mixtures thereof.

Volatile hydrocarbon-based oils that may be mentioned include $C_8$-$C_{16}$ isoparaffins such as the Isopar and Permethyl products, and especially isododecane, isooctane, isodecane and isohexadecane, and mixtures thereof.

Non-Volatile Solvent

Suitable non-volatile solvents include, but are not limited to, various types of oils. Mention may be made of hydrocarbon-based oils such as liquid paraffin or liquid petroleum jelly, mink oil, turtle oil, soybean oil, perhydrosqualene, sweet almond oil, beauty-leaf oil, palm oil, grapeseed oil, sesame seed oil, corn oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl alcohol or linolenyl alcohol, isostearyl alcohol or octyldodecanol; silicone oils such as polydimethylsiloxanes (PDMS), which are optionally phenylated such as phenyltrimethicones, trimethyl pentaphenyl siloxane, tetramethyl tetraphenyl siloxane, or optionally substituted with aliphatic and/or aromatic groups that are optionally fluorinated, or with functional groups such as hydroxyl, thiol and/or amine groups; polysiloxanes modified with fatty acids, with fatty alcohols, with polyoxyalkylenes or with hydrocarbyl functional groups, fluorosilicones and perfluoro oils.

The at least one solvent will typically be present in the composition of the invention in an amount of from 10 to 90% by weight, preferably from 20 to 80% by weight, more preferably from 30 to 70% by weight, and more preferably from 40 to 70% by weight, based on the weight of the composition.

Colorants

The composition according to the invention may also comprise at least one colorant. The colorant may be chosen from the lipophilic dyes, hydrophilic dyes, pigments and nacres usually used in cosmetic or dermatological compositions, and mixtures thereof. The colorant is generally present in an amount of from 0.1 to 50% by weight, preferably from 0.5 to 30% by weight, and more preferably from 1 to 20% by weight, based on the weight of the composition.

The liposoluble dyes may be selected, for example, from Sudan Red, D&C Red 17, D&C Green 6, p-carotene, Sudan brown, D&C Yellow 11, D&C Violet 2, D&C Orange 5, quinoline yellow and annatto, or mixtures thereof.

The pigments may be white or colored, mineral and/or organic, coated or uncoated, and of usual or nanometric size. The term "pigments" should be understood as meaning particles that are insoluble in the medium, intended to color and/or opacify the composition. Among the mineral pigments that may be mentioned are titanium dioxide, optionally surface-treated, zirconium oxide or cerium oxide and also iron oxide or chromium oxide, manganese violet, ultramarine blue, chromium hydrate and ferric blue, and mixtures thereof. Among the organic pigments that may be mentioned are carbon black, pigments of D&C type, and lakes based on cochineal carmine or on barium, strontium, calcium or aluminum, and mixtures thereof. The pigments may especially be coated with at least one silicone compound such as polydimethylsiloxanes and/or with polymers, especially polyethylenes and/or at least one fluoro compound and/or at least one amino acid. Mention may also be made of "SI oxides" which are polymethylhydrogenosiloxane-coated pigments sold by the company Miyoshi.

The nacreous pigments may be chosen from white nacreous pigments such as mica coated with titanium or with bismuth oxychloride, colored nacreous pigments such as titanium mica with iron oxides, titanium mica with, especially, ferric blue or chromium oxide, titanium mica with an organic pigment of the abovementioned type, and also nacreous pigments based on bismuth oxychloride, and mixtures thereof.

Other pigments which may be used include interference pigments and goniochromatic pigments such as those disclosed in US20040064509, the entire contents of which are incorporated by reference.

The film forming polypropylsilsesquioxane resin used in the compositions of the invention is incorporated into cosmetically acceptable compositions which may be anhydrous, or in the emulsion form. If the latter, the emulsion may be water-in-oil (W/O) or oil-in-water (0/W) or a multiple emulsion, such as, for example O/W/0 or W/O/W. Such emulsions will typically contain about 0.1-99% by weight water and 0.1-99% by weight oil, all weights being based on the weight of the composition.

Cosmetically Acceptable Additives

In addition to the above-mentioned ingredients, the cosmetic composition of the present invention may additionally contain various cosmetically acceptable additives.

Pasty Fatty Substance

The composition according to the invention may also contain at least one fatty compound that is pasty at room temperature. For the purposes of the invention, the expression "pasty fatty substance" means a compound with a melting point ranging from 25 to 60° C. and preferably from 30 to 45° C. and/or a hardness ranging from 0.001 to 0.5 MPa and preferably from 0.005 to 0.4 MPa.

The melting point values correspond to the melting point measured using a differential scanning calorimeter (DSC), such as the calorimeter sold under the name DSC 2920 by the company TA Instruments, with a temperature rise of 5 or 10° C. per minute. (The melting point considered is the point corresponding to the temperature of the most endothermic peak in the thermogram).

The hardness is measured according to a method of penetration of a probe into a sample of compound and in particular using a texture analyzer (for example the TA-XT21 from Rheo) equipped with a stainless steel cylinder 2 mm in diameter. The hardness measurement is performed at 20° C. at the center of 5 samples. The cylinder is introduced into each sample at a pre-speed of 1 mm/sec and then at a measuring speed of 0.1 mm/sec, the depth of penetration being 0.3 mm. The hardness value recorded is that of the maximum peak of the applied force.

According to the invention, one or more pasty fatty substances may also be used. Preferably, these fatty substances are hydrocarbon-based compounds, optionally of polymeric type; they may also be chosen from hydrocarbon-based compounds, silicone compounds and/or fluoro compounds, and mixtures thereof.

Among the pasty compounds that may be mentioned are lanolins and lanolin derivatives, for instance acetylated lanolins or oxypropylenated lanolins, with a viscosity from 18 to 21 Pa·s and preferably 19 to 20.5 Pa·s, and/or a melting point from 30 to 45° C., and mixtures thereof. Esters of fatty acids or of fatty alcohols may also be used, especially those containing 20 to 65 carbon atoms (melting point of about 20 to 35° C. and/or viscosity at 40° C. ranging from 0.1 to 40 Pa·s), for instance triisostearyl or cetyl citrate; arachidyl propionate; polyvinyl laurate; cholesterol esters, for instance triglycerides of plant origin such as hydrogenated plant oils, viscous polyesters, for instance poly(12-hydroxystearic acid), and mixtures thereof. Triglycerides of plant origin that may be used include hydrogenated castor oil derivatives, such as "Thixin R" from Rheox.

Mention may also be made of silicone pasty fatty substances such as polydimethylsiloxanes (PDMS) containing pendant chains of the alkyl or alkoxy type containing from 8 to 24 carbon atoms, and having a melting point of 20-55° C., for instance stearyl dimethicones, especially those sold by the company Dow Corning under the trade names DC2503 and DC2-5514, and mixtures thereof.

The pasty fatty substance may be present in an amount of from 0.1 to 70% by weight, preferably from 1 to 50% by weight, and more preferably from 2 to 30% by weight, based on the weight of the composition.

Additional Film Formers

The composition according to the invention may also contain at least one additional film-forming polymer chosen from liposoluble or lipodispersible film-forming polymers and mixtures thereof.

Liposoluble Polymer

The liposoluble polymers may be of any chemical nature and especially include:

1) liposoluble, amorphous homopolymers and copolymers of olefins, of cycloolefins, of butadiene, of isoprene, of styrene, of vinyl ethers, esters or amides, or of (meth)acrylic acid esters or amides comprising a linear, branched or cyclic $C_4$-$C_{50}$ alkyl group. The liposoluble homopolymers and copolymers may be chosen from those obtained from monomers chosen from the group consisting of isooctyl (meth)acrylate, isononyl (meth)acrylate, 2-ethylhexyl (meth)acrylate, lauryl (meth)acrylate, isopentyl (meth)-acrylate, n-butyl (meth)acrylate, isobutyl (meth)acrylate, tert-butyl (meth)acrylate, tridecyl (meth)acrylate and stearyl (meth)acrylate, or mixtures thereof. Examples that will be mentioned include the alkyl acrylate/cycloalkyl acrylate copolymer sold by PHOENIX CHEM under the name GIOVAREZ AC-5099 ML.

Liposoluble film-forming polymers that may also be mentioned include vinylpyrrolidone (VP) copolymers and especially copolymers of vinylpyrrolidone and of a $C_2$-$C_{40}$ and in particular $C_3$ to $C_{20}$ alkene. As examples of VP copolymers that may be used in the invention, mention may be made of copolymers of VP/vinyl acetate, VP/ethyl methacrylate, VP/ethyl methacrylate/methacrylic acid, VP/eicosene, VP/hexadecene, VP/triacontene, VP/styrene, VP/acrylic acid/lauryl methacrylate and butylated polyvinylpyrrolidone (PVP).

Particular liposoluble copolymers that may also be mentioned include:

i) liposoluble polymers belonging to one of the classes described above and bearing fluoro groups, in particular those described in patent U.S. Pat. No. 5,948,393 and the alkyl (meth)acrylate/perfluoroalkyl (meth)acrylate copolymers described in patents EP815836 and U.S. Pat. No. 5,849,318, the entire contents of which are incorporated by reference, ii) polymers or copolymers resulting from the polymerization or copolymerization of an ethylenic monomer, comprising one or more ethylenic bonds, which are preferably conjugated (or diene). This or these agent(s) is (are) in particular vinyl, acrylic or methacrylic copolymers, which may be in block form and especially of diblock or triblock type, or even of multiblock or starburst type.

The ethylenic film-forming polymer may especially comprise a styrene (S) block, an alkylstyrene (AS) block, an ethylene/butylene (EB) block, an ethylene/propylene (EP) block, a butadiene (B) block, an isoprene (I) block, an acrylate (A) block, a methacrylate (MA) block or a combination of these blocks.

In particular, the film-forming polymer used may be a copolymer comprising at least one styrene block. Most particularly, a triblock copolymer may be used and in particular those of the polystyrene/polyisoprene or polystyrene/polybutadiene type, such as those sold under the name "LUVITOL HSB" by BASF, and those of the polystyrene/copoly(ethylene-propylene) type or alternatively of the polystyrene/copoly(ethylene-butylene) type, such as those sold under the brand name "KRATON" by Shell Chemical Co. or Gelled Permethyl 99A by Penreco. Styrene-methacrylate copolymers may also be used.

As film-forming polymers that may be used in the composition of the invention, examples that may also be mentioned include KRATON G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton G1750X (EP) multiarm, Kraton G1765X (EP) multiarm, Kraton D-1101 (SBS), Kraton D-1102 (SBS), Kraton D-1107 (SiS), Gelled Permethyl 99A-750, Gelled Permethyl 99A-753-58 (blend of triblock and of starburst block polymer), Gelled Permethyl 99A-753-59 (blend of triblock and of starburst block polymer), Versagel 5970 and Versagel 5960 from Penreco (blend of triblock and of starburst polymer in isododecane), and OS129880, OS129881 and OS 84383 from Lubrizol (styrene-methacrylate copolymer);

2) amorphous liposoluble polysaccharides comprising alkyl (ether or ester) side chains, in particular alkylcelluloses comprising a linear or branched, saturated or unsaturated $C_1$-$C_8$ alkyl radical such as ethylcellulose and propylcellulose.

In general, the film-forming liposoluble polymers of the invention may have a weight-average molecular weight ranging from 1,000 to 500,000 and especially from 2,000 to 250,000, and a glass transition temperature ranging from $-100°$ C. to $+300°$ C., especially from $-50°$ C. to $+100°$ C. and in particular from $-10°$ C. to $+90°$ C.

Lipodispersible Polymer

The lipodispersible polymer is generally present in the form of a stable dispersion of particles, which are generally spherical and solid, in the liquid fatty phase. These dispersions may especially be in the form of polymer nanoparticles in dispersion. These nanoparticles may have a size ranging from 5 to 600 nm and especially ranging from 50 to 250 nm.

The dispersed polymer particles that may be used in the composition according to the invention may have a weight-average molecular weight ranging from about 2,000 to 10,000,000.

The polymer may have a glass transition temperature ranging from $-100°$ C. to $+300°$ C., especially from $-10°$ C. to $+50°$ C. and more particularly less than or equal to about $+40°$ C.

The polymer used in the present invention in the form of particles dispersed in the fatty phase may be of any nature. Thus, a free-radical polymer, a polycondensate, or even a polymer of natural origin, and blends thereof, may be used. The polymer may be chosen by a person skilled in the art on the basis of its properties.

It is more particularly a "film-forming" polymer, i.e. a polymer capable of forming, alone or in combination with a plasticizer, an isolable film.

Illustrations of film-forming polymers that may be mentioned include acrylic or vinyl free-radical homopolymers and copolymers, especially those with a glass transition temperature $T_g$ of less than or equal to about $+40°$ C. and in particular ranging from $-10°$ C. to $+30°$ C., and blends thereof.

The expression "free-radical polymer" means a polymer obtained by polymerization of monomers containing unsaturation, especially ethylenic unsaturation, each monomer being capable of homopolymerizing (unlike polycondensates). The free-radical polymers may especially be vinyl polymers or copolymers, especially acrylic polymers.

The vinyl polymers may result from the polymerization of ethylenically unsaturated monomers containing at least one acid group and/or esters of these acidic monomers and/or amides of these acids.

Monomers bearing an acidic group that may be used include $\alpha,\beta$-ethylenic unsaturated carboxylic acids such as acrylic acid, methacrylic acid, crotonic acid, maleic acid and itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), for instance (meth)acrylates of an alkyl, in particular of a $C_1$-$C_{20}$ and preferably $C_1$-$C_8$ alkyl, (meth)acrylates of an aryl, in particular of a $C_6$-$C_{10}$ aryl, (meth)acrylates of a hydroxyalkyl, in particular of a $C_2$-$C_6$ hydroxyalkyl.

Alkyl (meth)acrylates that may be mentioned include methyl, ethyl, butyl, isobutyl, 2-ethylhexyl and lauryl (meth)acrylate.

Hydroxyalkyl (meth)acrylates that may be mentioned include hydroxyethyl (meth)acrylate and 2-hydroxypropyl (meth)acrylate.

Aryl (meth)acrylates that may be mentioned include benzyl or phenyl acrylate.

Particularly advantageous (meth)acrylic acid esters are alkyl (meth)acrylates.

Free-radical polymers that may especially be used include copolymers of (meth)acrylic acid and of an alkyl (meth)acrylate, especially of a $C_1$-$C_4$ alkyl. More particularly, methyl acrylates optionally copolymerized with acrylic acid, such as copolymers of poly(methyl acrylate/acrylic acid) type, may be used.

Amides of the acidic monomers that may be mentioned include (meth)acrylamides, and especially N-alkyl(meth)acrylamides, in particular of a $C_2$-$C_{12}$ alkyl, such as N-ethylacrylamide, N-t-butylacrylamide and N-octylacrylamide, and N-di($C_1$-$C_4$)alkyl-(meth)acrylamides.

The vinyl polymers may also result from the polymerization of ethylenically unsaturated monomers containing at least one amine group, in free form or in partially or totally neutralized form, or alternatively in partially or totally quaternized form. Such monomers may be, for example, chosen from dimethylaminoethyl (meth)acrylate, dimethylaminoethylmethacrylamide, vinylamine, vinylpyridine or diallyldimethylammonium chloride.

The vinyl polymers may also result in the homopolymerization or copolymerization of at least one monomer chosen from vinyl esters and styrene monomers. In particular, these monomers may be polymerized with acidic monomers and/or esters thereof and/or amides thereof, such as those mentioned above.

Examples of vinyl esters that may be mentioned include vinyl acetate, vinyl propionate, vinyl neodecanoate, vinyl pivalate, vinyl benzoate and vinyl t-butylbenzoate.

Styrene monomers that may be mentioned include styrene and . α-methylstyrene.

The list of monomers given is not limiting and it is possible to use any monomer known to those skilled in the art falling within the categories of acrylic and vinyl monomers (including monomers modified with a silicone chain).

As other vinyl monomers that may be used, mention may also be made of:

N-vinylpyrrolidone, vinylcaprolactam, vinyl-N-($C_1$-$C_6$) alkylpyrroles, vinyloxazoles, vinylthiazoles, vinylpyrimidines and vinylimidazoles, and olefins such as ethylene, propylene, butylene, isoprene and butadiene.

The vinyl polymer may be crosslinked with the aid of difunctional monomers especially comprising at least two ethylenic unsaturations, such as ethylene glycol dimethacrylate or diallyl phthalate.

In a nonlimiting manner, the polymers of the invention may be chosen from the following polymers or copolymers: polyurethanes, polyurethane-acrylics, polyureas, polyurea-polyurethanes, polyester-polyurethanes, polyether-poly-urethanes polyesters, polyesteramides, alkyd fatty-chain polyesters; polyacrylamides; silicone polymers, fluoro polymers, and mixtures thereof.

According to one particular variant of the invention, the lipodispersible polymers may be surface-stabilized with at least one liposoluble polymer, for instance those described below or those described in patent application EP 1002528, the entire contents of which are incorporated by reference.

The film-forming polymer dispersion may be prepared as described in document EP749747 or in document EP1002528. More specifically, the polymerization is performed in dispersion, i.e. by precipitation of the polymer as it is formed, with protection of the formed particles with a stabilizer. Stabilizers are especially described in EP749747, the entire contents of which are incorporated by reference.

In general, the composition according to the invention may comprise from 0.1 to 30% by weight, preferably from 0.5 to 20% by weight, and more preferably from 1 to 15% by weight (expressed as solids), based on the weight of the composition, of a film-forming polymer and especially a lipodispersible film-forming polymer.

Structuring Agents

The composition of the invention may also contain structuring agents. Structuring agents are compounds which help with the integrity and the strength of the composition. Structuring agents may include waxes and polyamides.

i) Waxes

For the purposes of the present invention, a wax is a lipophilic fatty compound, which is solid at room temperature (25° C.) with a reversible solid/liquid change of state, having a melting point of greater than 45° C. and better still greater than 55° C., which may be up to 200° C., and having an anisotropic crystal organization in the solid state. For the purposes of this invention, the waxes are those generally used in cosmetics and dermatology. The waxes may be of natural origin, for instance beeswax, carnauba wax, candelilla wax, ouricoury wax, Japan wax, cork fiber wax or sugar cane wax, paraffin wax, lignite wax, microcrystalline waxes, lanolin wax, montan wax, ozokerites and hydrogenated oils, for instance hydrogenated jojoba oil. They may also be of synthetic origin, for instance polyethylene waxes derived from the polymerization of ethylene, waxes obtained by Fischer-Tropsch synthesis, esters of fatty acids and of glycerides that are solid at 40° C.

They may also be silicone waxes, referred to as alkyl, alkoxy or esters of poly(di)methylsiloxane silicones, which are polymers that comprise repeating dimethylsiloxy units in combination alkyl siloxy units wherein the long chain alkyl is generally a fatty chain that provides a wax-like character to the silicone. Such silicones include, but are not limited to stearoxydimethicone, behenoxy dimethicone, stearyl dimethicone, cetearyl dimethicone, and the like which are solid at 40° C. Waxes of synthetic origin are preferably used for reasons of greater reproducibility than waxes of natural origin.

i) Polyamides

Polyamides are compounds which result from the condensation, via an amide bond of carbonyl and amine groups. Substitution may be possible on the molecule, i.e. as a pendant chain on the molecule or on the terminal ends, or within the molecule, making it a copolymer.

Polyamide polymers resulting from the condensation of at least one aliphatic dicarboxylic acid and at least one diamine may be used Examples of these polyamide polymers are those sold under the brand name Versamid by the companies General Mills Inc. and Henkel Corp. (Versamid 930, 744 or 1655) or by the company Olin Mathieson Chemical Corp. under the brand name Omamid, in particular Omamid S or C. These resins have a weight-average molecular mass ranging from 6000 to 9000. For further information regarding these polyamides, reference may be made to U.S. Pat. Nos. 3,645,705 and 3,148,125, the entire contents of which are incorporated by reference.

Other examples of polyamides include those sold by the company Arizona Chemicals under the references Uni-Rez (2658, 2931, 2970, 2621, 2613, 2624, 2665, 1554, 2623 and 2662) and the product sold under the reference Macromelt 6212 by the company Henkel. These polyamides are described in U.S. Pat. No. 5,500,209, the entire contents of which are incorporated by reference. Such polyamides display high melt viscosity characteristics. MACROMELT 6212, for example, has a high melt viscosity at 190° C. of 30-40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins disclosed in U.S. Pat. Nos. 5,783,657 and 5,998,570, the entire contents of which are incorporated by reference.

Other structuring agents which may be used alone or in combination with the above are non silicone polyamides such as those known in the trade as Uniclear or Sylvaclear. These non silicone polyamides have different terminal end groups, such as ester terminated, known as Uniclear 80 or 100, such as amide terminated, known as Sylvaclear A200, and such as polyalkyleneoxy terminated, known as Sylvaclear AF1900 as well as ester terminated polyesteramides. These non silicone polyamides are available, for instance, from Arizona Chemical Company, Jacksonville, Fla., and are described in U.S. Pat. Nos. 5,783,657, 6,402,408, 6,268,466 and 6,552,160, the entire contents of which are incorporated by reference.

In the event that a structuring agent is employed, it may be present in the composition in an amount of from 0.1 to 30% by weight, preferably from 1 to 20% by weight, and more preferably from 2 to 15% by weight, based on the weight of the composition.

Organogelator

The composition of the invention may also comprise at least one organogelator. An organogelator is defined herein to include a non-polymeric organic compound whose molecules may be capable of establishing, between themselves, at least one physical interaction leading to a self-aggregation of the molecules with formation of a macromolecular 3-D network which may be responsible for the gelation of the liquid fatty phase. The network can result from the formation of a network of fibrils (due to the stacking or aggregation of organic-gelling molecules), immobilizing the molecules of the liquid fatty phase. Depending on the nature of the organogelator, the interconnected fibrils have variable dimensions which may range up to one micron, or even several microns. These fibrils may occasionally combine to form strips or columns.

The term "gelation" means a thickening of the medium which may result in a gelatinous consistency and even in a solid, rigid consistency which does not flow under its own weight. The ability to form this network of fibrils, and thus the gelation, depends on the nature (or chemical category) of the organogelator, the nature of the substituents borne by its molecules for a given chemical category, and the nature of the liquid fatty phase. For example, this gelation is reversible.

The physical interactions are diverse but may exclude co-crystallization. These physical interactions are, for instance, interactions chosen from self-complementary hydrogen interactions, it interactions between unsaturated rings, dipolar interactions, and coordination bonding with organometallic derivatives. The establishment of these interactions may often be promoted by the architecture of the molecule, such as by rings, unsaturations, and the presence of asymmetric carbons. In general, each molecule of an organogelator can establish several types of physical interaction with a neighboring molecule. Thus, in one embodiment, the molecules of the organogelator according to the invention may comprise at least one group capable of establishing hydrogen bonding, e.g., at least two groups capable of forming hydrogen bonding; at least one aromatic ring, e.g., at least two aromatic rings; at least one bond with ethylenic unsaturation; and/or at least one asymmetric carbon. The groups capable of forming hydrogen bonding may, for example, be chosen from hydroxyl, carbonyl, amine, carboxylic acid, amide and benzyl groups.

The organogelator of the invention may be soluble in the liquid fatty phase of the composition at room temperature and atmospheric pressure. It may be solid or liquid at room temperature and atmospheric pressure.

Organogelator(s) which can be used in the invention are, for example, those described in the document "Specialist Surfactants" edited by D. Robb, 1997, pp. 209-263, chapter 8, by P. Terech, and U.S. Pat. Nos. 6,372,235 and 6,726,195, the entire contents of which are incorporated by reference.

In the event that an organogelator is employed, it may be present in the composition in an amount of from 0.1 to 20_% by weight, preferably from 0.2 to 10% by weight, and more preferably from 0.5 to 5% by weight, based on the weight of the composition.

Gelling Agents

The composition of the invention may also contain at least one agent useful for gelling a liquid fatty phase. The gelling agent increases the liquid fatty phase viscosity and leads to a solid or flowable composition when introduced in said fatty phase. The gelling agent does not encompass waxes, in the sense that it is not waxy.

The at least one gelling agent may be chosen from gelling agents in polymeric form and gelling agents in mineral form.

In one embodiment, the at least one gelling agent is not soluble in an aqueous phase or in water.

The gelling agent according to the present invention is preferably selected from the group consisting of agents that gel via chemical reticulation and agents that gel via physical reticulation.

Gelling Agents that Gel Via Chemical Reticulation

According to one embodiment, crosslinked elastomeric polyorganosiloxanes of three-dimensional structure are preferred. These elastomeric silicones can bear hydrophilic groups, such as polyoxyethylene or copoly(oxyethylene/oxypropylene).

As elastomeric polyorganosiloxanes which can be used in the invention, mention may be made of the crosslinked elastomeric polyorganosiloxanes described in application EP295886A, the entire contents of which are incorporated by reference. According to that application, they are obtained by addition reaction and crosslinking, in the presence of a platinum-type catalyst, of at least:

(a) a polyorganosiloxane having at least two $C_2$ to $C_6$ lower alkenyl groups per molecule; and (b) a polyorganosiloxane having at least two hydrogen atoms linked to a silicon atom per molecule.

It is also possible to use the polyorganosiloxanes described in U.S. Pat. No. 5,266,321, the entire contents of which are incorporated by reference. According to that patent, they are chosen in particular from:

i) polyorganosiloxanes comprising $R_2SiO$ and $RSiO_{1.5}$ units and optionally $R_3SiO_{0.5}$ and/or $SiO_2$ units in which the radicals R, independently of each other, are chosen from a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1/1 to 30/1;

ii) polyorganosiloxanes which are insoluble and swellable in silicone oil, obtained by addition of an polyorganohydrogenosiloxane (1) and of a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic. Optionally, these polyorganosiloxanes can comprise from 1 to 40 oxyalkylene groups, such as oxypropylene and/or oxyethylene groups.

As examples of elastomeric polyorganosiloxanes which can be used according to the invention, mention may be made of those sold or made under the names KSG6 from Shin-Etsu, Trefil E-505C or Trefil E-506C from Dow-Corning, Gransil from Grant Industries (SR-CYC, SR DMF10, SR-DC556) or those marketed in the form of preconstituted gels (KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric or emulsifying elastomers such as those sold under the names of KSG-210, KSG-30, KSG-31, KSG-32, KSG-33, KSG-40, KSG 41, KSG-42, KSG-43 and KSG-44 from Shin-Etsu. A mixture of these commercial products may also be used.

Also available are cyclized dimethicones. The term "cyclized dimethicone" means an organosiloxane comprised of repeating —[$SiO_{2/2}$]—, or "D" units as defined previously, which form one or more cyclized portions in the final polymer. The cyclized portions, or rings, are formed by crosslinking certain portions along the organosiloxane chain to form rings that may be structurally aligned along the polymeric chain in the manner depicted below:

Preferably, the rings in the polymer have a molecular weight ranging from about 40,000 to 50,000, more preferably about 45,000, with the final polymer having a molecular weight ranging from about 1,600,000 to 2,600,000, preferably about 2,000,000. Cyclized dimethicone may be purchased from Jeen International under the tradename JEESILC IDD which is a mixture of cyclized dimethicone (having the INCI name dimethicone crosspolymer-3) and isododecane; or JEECHEM HPIB which is a mixture of cyclized dimethicone (dimethicone crosspolymer-3), hydrogenated polyisobutene, and cyclomethicone. The compositions of the invention may contain from about 0.1-95%, preferably about 0.5-80%, more preferably 1-75% by weight by the weight of total composition of the cyclized dimethicone. A mixture of these commercial products may also be used.

Gelling Agents that Gel Via Physical Reticulation

Gelling agents that gel via physical reticulation, in particular via molecular muddling, hydrogen interactions, sequences incompatibility or dipolar interactions, as well as liposoluble polymers having liquid crystal groups, are preferred.

Gelling agents that gel via molecular muddling are polymers having high molecular weights, preferably higher than 500 000, such as silicone gums.

The silicone gum can correspond to the formula:

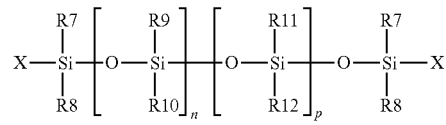

in which:

$R_7$, $R_8$, $R_{11}$ and $R_{12}$ are identical or different, and each is chosen from alkyl radicals comprising from 1 to 6 carbon atoms, $R_9$ and $R_{10}$ are identical or different, and each is chosen from alkyl radicals comprising from 1 to 6 carbon atoms and aryl radicals, X is chosen from alkyl radicals comprising from 1 to 6 carbon atoms, a hydroxyl radical and a vinyl radical, n and p are chosen so as to give the silicone gum a viscosity of greater than 100000 mPa·s, such as greater than 500000 mPa·s.

In general, n and p can each take values ranging from 0 to 5000, such as from 0 to 3000.

Among the silicone gums which can be used according to the invention, mention may be made of those for which:

the substituents $R_7$ to $R_{12}$ and X represent a methyl group, p=0 and n=2700, such as the product sold or made under the name SE30 by the company General Electric, the substituents $R_7$ to $R_{12}$ and X represent a methyl group, p=0 and n=2300, such as the product sold or made under the name AK 500000 by the company Wacker, the substituents $R_7$ to $R_{12}$ represent a methyl group, the substituent X represents a hydroxyl group, p=0 and n=2 700, as a 13% solution in cyclopentasiloxane, such as the product sold or made under the name Q2-1401 by the company Dow Corning, the substituents $R_7$ to $R_{12}$ represent a methyl group, the substituent X represents a hydroxyl group, p=0 and n=2 700, as a 13% solution in polydimethylsiloxane, such as the product sold or made under the name Q2-1403 by the company Dow Corning, and the substituents $R_7$, $R_8$, $R_{11}$, $R_{12}$ and X represent a methyl group and the substituents $R_9$ and $R_{10}$ represent an aryl group, such that the molecular weight of the gum is about 600 000, for instance the product sold or made under the name 761 by the company Rhone-Poulenc (Rhodia Chimie).

In preferred embodiments, the silicone gum correspond to the following formula:

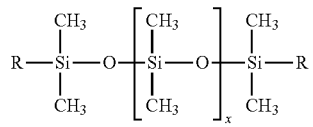

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cyclohexyl, phenyl, fluoroalkyl, and mixtures thereof. The silicone gums employed in the present invention may be terminated by triorganosilyl groups of the formula R'$_3$ where R' is a radical of monovalent hydrocarbons containing from 1 to 6 carbon atoms, hydroxyl groups, alkoxyl groups and mixtures thereof. The silicone gums used in the invention have an affinity with the structuring polymer and/or with the silicone gum, and the liquid fatty phase, the polymer and the silicone gum form a physiologically acceptable medium.

A particularly preferred fluid diorganopolysiloxane polymer is poly(dimethylsiloxane), herein referred to as PDMS. Also useful is a mixture of silicone gums such as the commercially available DC 1503 which is a blend of dimethicone and dimethiconol. Other useful silicone gums are DC 1428 fluid (Dow Corning) and those silicone gums described in U.S. Pat. No. 4,574,082, the entire contents of which are incorporated by reference.

In certain embodiments of the present invention, crystalline silicone compounds are included in the compositions.

A crystalline silicone compound is a compound comprising silicone in its molecule, which is solid at room temperature, and has a crystalline character.

The crystalline silicone compounds belong to a class of alkyl siloxane waxes corresponding to the formulae below:

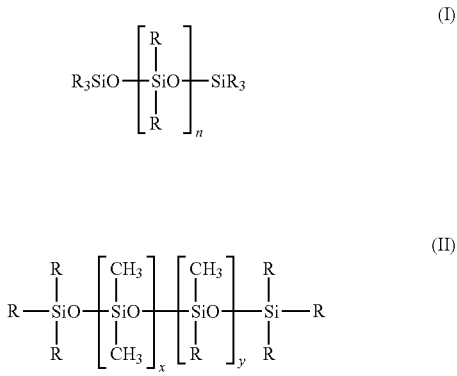

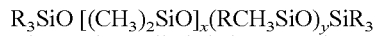

This could also be written as

R$_3$SiO [(CH$_3$)$_2$SiO]$_x$(RCH$_3$SiO)$_y$SiR$_3$ where R is an alkyl chain. x may be 0. The substituent R may be as low as 1 or as high as 50 or more as long as this silicone compound crystallizes at room temperature.

Examples of crystalline silicone compounds include, but are not limited to, C20-24 Alkyl Methicone, C24-28 Alkyl Dimethicone, C20-24 Alkyl Dimethicone, C24-28 Alkyl Dimethicone commercially available from Archimica Fine Chemicals, Gainesville, Fla. under the designation of SilCare 41M40, SilCare 41M50, SilCare 41M70 and SilCare 41M80. Stearyl Dimethicone available as SilCare 41M65 from Archimica or as DC-2503 from Dow-Corning, Midland, Mich. Similarly, stearoxytrimethylsilane sold as SilCare 1M71 or DC-580 may be used in an embodiment of this invention. Furthermore, similar crystalline compounds are available from Degussa Care Specialties, Hopewell, Va. under the designation ABIL Wax 9810, 9800, or 2440, or Wacker-Chemie GmbH, Burghausen, Germany, under the designation BelSil SDM 5055, or OSi Specialties, Greenwich, Conn. under the designation Silsoft. Other crystalline silicone compounds include C30-45 Alkyl Methicone available from Dow Corning as AMS-C30 Wax, as well as GE's SF1642, or SF-1632 available from General Electric, Fairfield, Conn.

In another embodiment, the at least one gelling agent may be in mineral form with particle sizes that cause little or no light scattering. Thus, it may be possible to obtain a translucent or even transparent composition.

As modified clays which can be used, mention may be made of hectorites modified with an ammonium chloride of a C$_{10}$ to C$_{22}$ fatty acid, such as hectorite modified with distearyldimethylammonium chloride, also known as quaternium-bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as steralkonium bentonites, such as the products sold or made under the names Claytone APA and Claytone AF by the company Southern Clay, and Baragel 24 sold or made by the company Rheox.

As other mineral gelling agents, which can be used in the invention, mention may be made of silica, such as fumed silica. The fumed silica may have a particle size, which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica.

The hydrophobic groups may be:

trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot;

groups derived from reacting fumed silica with silane alkoxides or siloxanes. These treated silicas are, for example, the products sold or made under the reference "Aerosil R805®" by the company Degussa.

Hydrophobic silica, such as fumed silica, may be used as lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one liposoluble gelling agent can allow the exudation of the composition to be limited and can allow its stability to be increased, while at the same time conserving the composition's glossy appearance, which is not possible with waxes such as those used conventionally in cosmetics and dermatology.

In the event that a gelling agent is employed, it may be present in the composition in an amount of from 0.1 to 40% by weight, preferably from 0.5 to 30% by weight, and more preferably from 1 to 20% by weight, based on the weight of the composition.

Emollients

Another useful component of cosmetic compositions is an emollient. These emollients may be silicone compatible oils that mimic or are compatible with a lipophilic content generally found within skin or hair. A preferred emollient is squalane. However, many traditional silicone compatible oils may be used. Useful emollients include, but are not limited to fatty bodies liquid at ambient temperature, such as esters, mineral oils, animal oils, vegetable oils, synthetic oils, and silicone oils. Examples of useful esters include, but are not limited to, isononyl isononanoate, octyl palmitate, cetyl lactate, pentaerythrityl tetraoctanoate, tridecyl octanoate, tridecyl behenate, isopropyl jojobate and jojoba alcohols, butyloctyl salicylate, polyglyceryl-3 diisostearate, tridecyl trimellitate, tridecyl stearate, and neopentylglycol dicaprylate/dicaprate. In one embodiment of the invention, the esters are chosen from isononyl isononanoate, a light ester which adds to the initial feel of the inventive composition on the skin, and pentaerythrityl tetraoctanoate, an ester which helps to cushion after the makeup is blended into the skin. Examples of useful oils include, but are not limited to, petrolatum oil, liquid lanolin, arara oil, sesame oil, macadamia oil, jojoba oil, silicone oils such as phenyl trimethicone and dimethicone, and synthetic triglycerides such as capric caprylic triglyceride and hydrogenated cocoglycerides.

The silicone compatible organic oil which may be used as emollients also include esters, hydrocarbon oils, or an animal, vegetable, or mineral oils. The term compatible means that the organic oil is soluble or dispersible in the silicone mixture to form a stable solution or dispersion. Esters include mono-, di-, and triesters. The composition may comprise one or more esters selected from the group, or mixtures thereof. Preferably the composition contains a mixture of di- and triesters. Monoesters are defined as esters formed by the reaction of a monocarboxylic acid having the formula R—COOH, wherein R is a straight or branched chain saturated or unsaturated alkyl having 2 to 30 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups, and in one preferred embodiment of the invention the acid is an alpha hydroxy acid. Either one or both of the acid or alcohol may be a fatty acid or alcohol, i.e. may have from about 6 to 22 carbon atoms. Examples of monoester oils that may be used in the compositions of the invention include hexyl decyl benzoate, hexyl laurate, hexadecyl isostearate, hexyldecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, cetyl octanoate, cetyl laurate, cetyl lactate, cetyl isononanoate, cetyl stearate, stearyl lactate, stearyl octanoate, stearyl heptanoate, stearyl stearate, and so on. It is understood that in the above nomenclature, the first term indicates the alcohol and the second term indicates the acid in the reaction, i.e. stearyl octanoate is the reaction product of stearyl alcohol and octanoic acid. Preferred is monoester which is the reaction product of an aliphatic $C_{2-8}$ alcohol and a $C_{14-22}$ fatty acid, more particularly, the reaction product of a hexyl alcohol and lauric acid, also referred to as hexyl laurate.

Suitable diesters that may be used in the compositions of the invention are the reaction product of a dicarboxylic acid and an aliphatic or aromatic alcohol. The dicarboxylic acid may contain from 2 to 30 carbon atoms, and may be in the straight or branched chain, saturated or unsaturated form. The dicarboxylic acid may be substituted with one or more hydroxyl group. The aliphatic or aromatic alcohol may also contain 2 to 30 carbon atoms, and may be in the straight or branched chain, saturated, or unsaturated form. The aliphatic or aromatic alcohol may be substituted with one or more substituents such as hydroxyl. Preferably, one or more of the acid or alcohol is a fatty acid or alcohol, i.e. contains 14-22 carbon atoms. The dicarboxylic acid may also be an alpha hydroxy acid. Examples of diester oils that may be used in the compositions of the invention include diisostearyl malate (the reaction product of isostearic alcohol and malic acid), neopentyl glycol dioctanoate (the reaction product of neopentyl glycol and 2-ethyl hexanoic acid), dibutyl sebacate (reaction product of butyl alcohol and sebacic acid), di-$C_{12-13}$ alkyl malate (reaction product of $C_{12-13}$ alcohol and malic acid), dicetearyl dimer dilinoleate (reaction product of cetearyl alcohol and adipic acid), dicetyl adipate (reaction product of cetyl alcohol and adipic acid), diisocetyl adipate (reaction product of hexadecyl alcohol and adipic acid), diisononyl adipate (reaction product of isononyl alcohol and adipic acid), diisostearyl dimer dilinoleate (reaction product of isostearyl alcohol and dilinoleic acid), disostearyl fumarate (reaction product of isostearyl alcohol and fumaric acid), and so on.

Suitable triesters comprise the reaction product of a tricarboxylic acid and an aliphatic or aromatic alcohol. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 14 to 22 carbon atoms.

Examples of triesters include triarachidin (reaction product of glycerin and arachidic acid), tributyl citrate (reaction product of butyl alcohol and citric acid), tri $C_{12-13}$ alkyl citrate (reaction product of $C_{12-13}$ alcohol and citric acid), tricaprylin (reaction product of glycerin and caprylic acid), tricaprylyl citrate (reaction product of capryl alcohol and citric acid), tridecyl behenate (reaction product of tridecyl alcohol and behenic acid), trioctyldodecyl citrate (reaction product of octyldodecyl alcohol and citric acid), tridecyl behenate (reaction product of tridecyl alcohol and behenic acid), tridecyl cocoate (reaction product of tridecyl alcohol and coconut acid), tridecyl isononanoate (reaction product of tridecyl alcohol and isononanoate), and so on. Preferred is a triester which is the reaction product of an alpha hydroxy acid and a guerbet alcohol having 6 to 30 carbon atoms, in particular the reaction product of citric acid and octyldodecyl alcohol, referred to as trioctyldodecyl citrate.

In the event that an emollient is employed, it may be present in the composition in an amount of from 0.1 to 80% by weight, preferably from 1 to 70% by weight, and more preferably from 2 to 60% by weight, based on the weight of the composition.

Hydrating Agents and Skin Conditioning Agents

Suitable hydrating agents and skin conditioning agents may include hydroxyl-containing compounds such as polyols, polymeric or monomeric ethers, dihydric alcohols, as well as cationic agents and the like.

Polyols

Polyols are suitable hydrating agents. For purposes of this specification, polyols are defined as compounds which contain three or more hydroxyl groups per molecule. Examples of suitable polyols include fructose, glucamine, glucose, glucose glutamate, glucuronic acid, glycerin, 1,2,6 hexanetriol, hydroxystearyl methylglucanine, inositol, lactose, maltitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mixtures thereof. An especially preferred polyol is glycerin.

Dihydric Alcohols

Also suitable for use as hydrating agents are dihydric alcohols of the general formula $R(OH)_n$ where n is 2 and R is a substituted or unsubstituted saturated $C_2$-$C_{10}$, preferably $C_1$-$C_8$ alkyl, or a substituted or unsubstituted alicyclic, bicyclic, or aromatic ring, with the substituents selected from halogen, alkoxy, hydroxy, and so on. Examples of suitable alcohols include hexylene glycol, diethylene glycol, ethylene glycol, propylene glycol, 1,2-butylene glycol, triethylene glycol, dipropylene glycol, and mixtures thereof.

Polymeric or Monomeric Ethers

Also suitable as hydrating agents are homopolymeric or block copolymeric liquid ethers. Polymeric ethers are preferably formed by polymerization of monomeric alkylene oxides, generally ethylene or propylene oxides. Examples of such polymeric ethers include PEG, PPG, and derivatives thereof.

Other examples of suitable polymeric ethers include polyoxypropylene polyoxyethylene block copolymers. Such compounds are sold under the CTFA name Meroxapol 105, 108, 171, 172, 174, 178, 251, 252, 254, 255, 258, 311, 312, and 314.

In the event that a hydroxyl-containing hydrating/skin conditioning agent is employed, it may be present in the composition in an amount of from __0.01__ to 20_% by weight, preferably from __0.5__ to 15_% by weight, and more preferably from __1__ to __10_% by weight, based on the weight of the composition.

Cationic Skin Conditioning Agents

Cationic skin conditioning agents may include cationic polymers such as cationic polysaccharides selected from the group consisting of celluloses, guars, their derivatives and their mixtures. Cationic cellulose is available from Amerchol Corp. (Edison, N.J., USA) in their Polymer JR™ and LR™ series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Another suitable type of cationic polysaccharide that can be used is a cationic guar gum derivative, such as guar hydroxypropyltrimonium chloride (Commercially available from Rhone-Poulenc in the JAGUAR™ series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

In the event that a cationic hydrating/skin conditioning agent is employed, it may be present in the composition in an amount of from 0.01 to 2% by weight, preferably from 0.1 to 1.5% by weight, and more preferably from 0.2 to 1% by weight, based on the weight of the composition.

Fillers

The composition may also contain at least one filler, especially in order to obtain a matt product, which is especially desired for foundations and in particular for foundations or day creams for individuals with greasy skin. The term "filler" means any particle that is solid at room temperature and atmospheric pressure, used alone or in combination, which does not react chemically with the various ingredients of the composition and which are insoluble in these ingredients, even when these ingredients are brought to a temperature above room temperature and especially to their softening point or to their melting point. These inert fillers have melting points at least higher than 170° C. and better still higher than 200° C. They may be absorbent or nonabsorbent, i.e. capable in particular of absorbing the oils of the composition and also the biological substances secreted by the skin. Preferably, these fillers have an apparent diameter ranging from 0.01 to 150 μm, preferably from 0.5 to 120 μm and better still ranging from 1 to 80 μm. An apparent diameter corresponds to the diameter of the circle in which the elementary particle is inscribed along its smallest dimension (thickness for lamellae)

The fillers that may be used in the composition according to the invention may be mineral or organic, lamellar, spherical or oblong. Mention may be made of talc, mica, silica, kaolin, polyamide powders, for instance Nylon®. (Orgasol® from Atochem), poly-β-alanine powders, polyethylene powders, powders of an acrylic polymer and especially of polymethyl methacrylate (PMMA), for instance the product sold by Wackherr under the reference Covabead LH-85 (particle size 10-12 μm), powders of acrylic acid copolymers (Polytrap® from Dow Corning), polytetrafluoroethylene (Teflon®) powders, lauroyllysine, boron nitride, starch, hollow polymer microspheres such as those of polyvinylidene chloride/acrylonitrile, for instance Expancel® (Nobel Industrie), carbonates such as precipitated calcium carbonate, magnesium carbonate and magnesium hydrocarbonate, hydroxyapatite, hollow silica microspheres (Silica Beads® from Maprecos), hollow silica ellipsoids (Silica Shells from Kobo), glass microcapsules, ceramic microcapsules and polyester particles, and mixtures thereof. These fillers may be surface-treated, especially to make them lipophilic.

In the event that a filler is employed, it may be present in the composition in an amount of from 0.1 to 50% by weight, preferably from 1 to 40% by weight, and more preferably from 2 to 30% by weight, based on the weight of the composition.

Surfactants

The composition according to the invention may contain a surfactant or a mixture of surfactants, especially a surfactant whose HLB (hydrophilic/lipophilic balance) value allows the production of a water-in-oil (W/O) or oil-in-water (O/W) emulsion.

As surfactants that may be used, suitable for obtaining a W/O emulsion, mention may be made of those with an HLB value of less than 7, and especially fatty acid esters of polyols, for instance mono-, di-, tri- or sesquioleates or stearates of sorbitol or of glycerol, glyceryl laurate or polyethylene glycol laurate; alkyl or alkoxy dimethicone copolyols with an alkyl or alkoxy chain pendant or at the end of the silicone skeleton, containing, for example, from 6 to 22 carbon atoms.

As surfactants that may be used to obtain an 0/W emulsion, mention may be made of those with an HLB value of greater than 7, for instance fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl) ethers and dimethicone copolyols; and mixtures thereof. In general, any amphoteric ionic (cationic or anionic) surfactant and any nonionic surfactant that is well known to those skilled in the art may be used.

In the event that a surfactant is employed, it may be present in the composition in an amount of from 0.1 to 20% by weight, preferably from 0.5 to 15% by weight, and more preferably from 1 to 10% by weight, based on the weight of the composition.

The composition of the invention may also comprise any additive conventionally used in the field of cosmetics such as, for example, antioxidants, essential oils, preserving agents, fragrances, neutralizers, cosmetic or dermatological active agents such as, for example, vitamins, essential fatty acids, sunscreens, free-radical scavengers, dispersants, anti-acne agents and mixtures thereof. These additives may be present in the composition in an amount of from 0.01 to 10% by weight, preferably from 0.1% to 8% by weight, and more preferably from 0.5 to 5% by weight, based on the total weight of the composition. Advantageously, the composition contains at least one cosmetic or dermatological active agent.

Needless to say, a person skilled in the art will take care to select the optional additional additives and/or the amount thereof such that the advantageous properties of the composition according to the invention are not, or are not substantially, adversely affected by the envisaged addition.

EXAMPLES

The present invention will be better understood from the examples which follow, all of which are intended for illustrative purposes only, and are not meant to unduly limit the scope of the invention in any way.

Inventive and comparative examples of lipstick compositions were made as follows:

| Phase | Ingredient | Comparative | Inventive |
|---|---|---|---|
| A | Isododecane | 67.00 | 62.00 |
|  | Resin MK (Polymethylsilsesquioxane) | 20.00 |  |
|  | DC 670 (80% w/w Polypropylsilsesquioxane) in isododecane |  | 25.00 |
|  | Polyethylene wax (Performalene 400) | 3.00 | 3.00 |
| B | Black Iron Oxide | 0.83 | 0.83 |
|  | Red Iron Oxide | 1.57 | 1.57 |
|  | D&C Red #7 | 1.42 | 1.42 |
|  | Titanium Dioxide | 4.71 | 4.71 |
|  | Yellow #5 Al. Lake | 1.47 | 1.47 |
|  | TOTAL | 100.00 | 100.00 |

Preparation Procedure:
1. Combine Phase A ingredients together in a beaker and heat to 100° C. using an oil bath; Mix with a propeller mixer until the polyethylene wax is completely melted and the mixture is uniform.
2. Combine Phase B ingredients together into Phase A, then transfer the mixture to a Disconti Ball Mill and mill the mixture for about 30 minutes.
3. Transfer the resulting fluid to individual packages.

The resulting compositions had a fluid paste like consistency. The lip compositions were applied to the lips of 6 panelists. The lips were photographed before, and immediately after, application using diffuse lighting in a device such as the one described and claimed in US20030067545, the entire contents of which are incorporated by reference, and the images analyzed for L* color value. The L* color value indicates the darkness or intensity of the color. The panelists were then asked to eat a meal consisting of a sandwich, a salad and a hot beverage. The lips of the panelists were photographed after the meal using the device above, and the images analyzed for L* color value. The wear is reported as % wear and indicates how much of the composition remains on the lips.

The results are shown in the following table:

|  | No. of panelists | % Wear after meal |
|---|---|---|
| Comparative example | 6 | 36.8 +/− 20.3 |
| Inventive example | 6 | 80.6 +/− 13.0 |

These results indicate that the inventive composition containing a polypropylsilsesquioxane film forming resin performed in a superior way in terms of wear properties when compared to a composition containing a polymethylsilsesquioxane film forming resin.

What is claimed is:

1. A cosmetic composition comprising:
   (a) at least one polypropylsilsesquioxane film forming resin;
   (b) at least one volatile solvent; and
   (c) optionally, at least one colorant,
wherein the cosmetic composition is anhydrous and is free from any non-volatile solvent or plasticizer.

2. The composition of claim 1 wherein the at least one polypropylsilsesquioxane is present in an amount of from about 0.5 to about 80% by weight, based on the weight of the composition.

3. The composition of claim 1 wherein the at least one polypropylsilsesquioxane is present in an amount of from about 20 to about 30% by weight, based on the weight of the composition.

4. The composition of claim 1 wherein the at least one solvent is present in an amount of from about 10 to about 90% by weight, based on the weight of the composition.

5. The composition of claim 1 wherein the at least one solvent is present in an amount of from about 40 to about 70% by weight, based on the weight of the composition.

6. The composition of claim 1 wherein the at least one colorant is present in an amount of from about 0.1 to about 50% by weight, based on the weight of the composition.

7. The composition of claim 1 wherein the at least one colorant is present in an amount of from about 1 to about 20% by weight, based on the weight of the composition.

8. The composition of claim 1 wherein the composition is a lipstick.

9. The composition of claim 1 wherein the composition is a foundation.

10. The composition of claim 1 wherein the composition is a mascara.

11. A process for treating a keratinous material comprising:
(a) providing a keratinous material;
(b) providing a cosmetic composition containing:
   (i) at least one polypropylsilsesquioxane film forming resin;
   (ii) at least one volatile solvent;
   (iii) and optionally, at least one colorant;
   wherein the cosmetic composition is anhydrous and is free from any non-volatile solvent or plasticizer; and
(c) applying the cosmetic composition onto the keratinous material.

12. The process of claim 11 wherein the at least one polypropylsilsesquioxane is present in an amount of from about 0.5 to about 80% by weight, based on the weight of the composition.

13. The process of claim 11 wherein the at least one polypropylsilsesquioxane is present in an amount of from about to about 30% by weight, based on the weight of the composition.

14. The process of claim 11 wherein the at least one solvent is present in an amount of from about 10 to about 90% by weight, based on the weight of the composition.

15. The process of claim 11 wherein the at least one solvent is present in an amount of from about 40 to about 70% by weight, based on the weight of the composition.

16. The process of claim 11 wherein the at least one colorant is present in an amount of from about 0.1 to about 50% by weight, based on the weight of the composition.

17. The process of claim 11 wherein the at least one colorant is present in an amount of from about 1 to about 20% by weight, based on the weight of the composition.

18. The process of claim 11 wherein the composition is a lipstick.

19. The process of claim 11 wherein the composition is a foundation.

20. The process of claim 11 wherein the composition is a mascara.

* * * * *

UNITED STATES PATENT AND TRADEMARK OFFICE
CERTIFICATE OF CORRECTION

| | | |
|---|---|---|
| PATENT NO. | : 8,025,869 B2 | Page 1 of 2 |
| APPLICATION NO. | : 11/168796 | |
| DATED | : September 27, 2011 | |
| INVENTOR(S) | : Wei Hong Yu | |

It is certified that error appears in the above-identified patent and that said Letters Patent is hereby corrected as shown below:

On the Title page, Item 57, line 1, "provides" should read -- provide --.
On the Title page, Item 57, line 3, "film forming" should read -- film-forming --.
Column 1, line 39, "film forming" should read -- film-forming --.
Column 1, line 42, "film forming" should read -- film-forming --.
Column 1, line 47, "film forming" should read -- film-forming --.
Column 1, line 54, "film forming" should read -- film-forming --.
Column 1, line 60, "film forming" should read -- film-forming --.
Column 2, line 6, "film forming" should read -- film-forming --.
Column 2, line 8, "film forming" should read -- film-forming --.
Column 2, line 21-22, "film forming" should read -- film-forming --, both occurrences.
Column 2, line 24, "film forming" should read -- film-forming --.
Column 2, line 54, after "oxygen" insert -- atom --.
Column 3, line 59, "film forming" should read -- film-forming --.
Column 3, line 64, "film former" should read -- film-former --.
Column 3, line 66, "film former" should read -- film-former --.
Column 4, line 4, "film forming" should read -- film-forming --.
Column 4, line 14, "comprises" should read -- comprise --.
Column 4, line 19, "film forming" should read -- film-forming --.
Column 5, line 62, "film forming" should read -- film-forming --.
Column 10, line 50, after "to" insert -- , --.
Column 10, line 64, after "used" insert -- . --.
Column 11, line 27, "non silicone" should read -- non-silicone --.
Column 11, line 31, "non silicone" should read -- non-silicone --.
Column 14, line 50, "correspond" should read -- corresponds --.
Column 17, line 20, after "to" insert -- , --.
Column 22, line 10, "paste like" should read -- paste-like --.
Column 22, line 33, "film forming" should read -- film-forming --.
Column 22, line 36, "film forming" should read -- film-forming --.
Column 22, line 40, "film forming" should read -- film-forming --.

Signed and Sealed this
Fourth Day of December, 2012

David J. Kappos
*Director of the United States Patent and Trademark Office*

CERTIFICATE OF CORRECTION (continued)
U.S. Pat. No. 8,025,869 B2

Column 23, line 8, "film forming" should read -- film-forming --.
Column 23, line 21, after "about" insert -- 20 --.